United States Patent
Le

(10) Patent No.: US 6,850,314 B2
(45) Date of Patent: Feb. 1, 2005

(54) METHOD FOR OPTICAL SENSING

(75) Inventor: Han Quang Le, Houston, TX (US)

(73) Assignee: Board of Reagents University of Houston, Houston, TX (US)

(*) Notice: Subject to any disclaimer, the term of this patent is extended or adjusted under 35 U.S.C. 154(b) by 0 days.

(21) Appl. No.: 10/637,367

(22) Filed: Aug. 8, 2003

(65) Prior Publication Data
US 2004/0033616 A1 Feb. 19, 2004

Related U.S. Application Data

(60) Provisional application No. 60/401,581, filed on Aug. 8, 2002.

(51) Int. Cl.[7] .............................. G01C 3/08; G01C 3/00; G01N 21/00
(52) U.S. Cl. ......................... 356/5.11; 356/3.1; 356/4.1; 356/343
(58) Field of Search ............................... 356/3.01–5.15, 356/343

(56) References Cited

U.S. PATENT DOCUMENTS

| | | | |
|---|---|---|---|
| 4,725,147 A | 2/1988 | Stoddart | 356/433 |
| 4,768,516 A | 9/1988 | Stoddart et al. | 128/665 |
| 4,814,604 A | 3/1989 | Lequime | 250/227 |
| 4,817,623 A | 4/1989 | Stoddart et al. | 128/665 |
| 5,140,989 A | 8/1992 | Lewis et al. | 128/665 |
| 5,187,672 A | 2/1993 | Chance et al. | 364/550 |
| 5,191,458 A | 3/1993 | Lyons et al. | 359/127 |
| 5,217,013 A | 6/1993 | Lewis et al. | 128/633 |
| 5,282,467 A | 2/1994 | Piantadosi et al. | 128/633 |
| 5,299,869 A | 4/1994 | Wissinger | 374/137 |
| 5,307,146 A | 4/1994 | Porter et al. | 356/320 |
| 5,353,799 A | 10/1994 | Chance | 128/664 |
| 5,381,010 A | 1/1995 | Gordon | 250/343 |
| 5,421,329 A | 6/1995 | Casciani et al. | 128/633 |
| 5,555,268 A | 9/1996 | Fattouche et al. | 375/206 |
| 5,564,832 A | 10/1996 | Ball et al. | 374/161 |
| 5,697,367 A | 12/1997 | Lewis et al. | 128/633 |
| 5,774,215 A | 6/1998 | Padgett et al. | 356/346 |
| 5,779,631 A | 7/1998 | Chance | 600/328 |
| 5,782,237 A | 7/1998 | Casciani et al. | 128/633 |
| 5,792,051 A | 8/1998 | Chance | 600/310 |
| 5,795,292 A | 8/1998 | Lewis et al. | 600/323 |
| 5,853,370 A | 12/1998 | Chance et al. | 600/473 |
| 5,902,235 A | 5/1999 | Lewis et al. | 600/323 |
| 6,075,610 A | * 6/2000 | Ueda et al. | 356/432 |
| 6,335,792 B1 | * 1/2002 | Tsuchiya | 356/432 |
| 6,516,214 B1 | 2/2003 | Boas | 600/431 |
| 6,577,884 B1 | 6/2003 | Boas | 600/310 |
| 2002/0131163 A1 | 9/2002 | Hasson et al. | 359/343 |
| 2003/0067537 A1 | 4/2003 | Myers | 348/47 |
| 2003/0076485 A1 | 4/2003 | Ruff et al. | 356/5.09 |
| 2003/0137647 A1 | 7/2003 | Hasson et al. | 356/5.01 |

* cited by examiner

Primary Examiner—Bernarr E. Gregory
Assistant Examiner—Brian Andrea
(74) Attorney, Agent, or Firm—Tim Headley; Gardere Wynne Sewell LLP

(57) ABSTRACT

A method for determining optical properties of a target, using a plurality of transmitters for transmitting signals at the target, and a plurality of receivers for detecting reflected signals from the target, comprises the steps of: a) transmitting radiation signals with a plurality of wavelengths at the target; b) detecting trace reflected radiation signals from the target; c) modulating the plurality of transmitters with a waveform for generating transmitter modulation codes; d) mixing the transmitter modulation codes with the trace reflected radiation signals to generate total signals; e) transmitting the total signals at the target; f) detecting reflected total signals from the target; g) digitizing the reflected total signals with an analog-digital converter to generate digitized signals; h) integrating the digitized signals with decoding functions to extract individual signals from the total signals; and i) determining the optical properties of the target from the individual signals.

10 Claims, 5 Drawing Sheets

METHOD FOR OPTICAL SENSING

CROSS-REFERENCES TO RELATED APPLICATIONS

This application claims the benefit of U.S. provisional patent application No. 60/401,581, filed Aug. 8, 2002.

STATEMENT REGARDING FEDERALLY SPONSORED RESEARCH OR DEVELOPMENT

The U.S. Government has a paid-up license in this invention, and the right in limited circumstances to require the patent owner to license others on reasonable terms as provided for by the terms of contract number 1-5-51704 awarded by DARPA/MTO.

REFERENCE TO A "SEQUENTIAL LISTING," A TABLE, OR A COMPUTER PROGRAM LISTING APPENDIX SUBMITTED ON A COMPACT DISC

Not Applicable.

BACKGROUND OF THE INVENTION

1. Field of the Invention

This invention pertains to active optical sensing systems, and more particularly, to ladars and diffuse optical tomography.

2. Description of Related Art

There are at least two types of active optical sensing systems: ladars and diffuse optical tomography systems. A typical ladar system includes a light source, which is a transmitter, and a detector, which is a receiver. The transmitter can be a coherent or incoherent source. The receiver can be a simple detector or a performance-enhanced detector. Some ladars are designed to measure the spectral properties of a subject. The transmitter is a wavelength-tunable laser or multiple lasers of different wavelengths. By comparing the relative absorption by the target at different wavelengths, the system can infer the medium properties. In a wavelength-tunable single-frequency laser transmitter, only one wavelength can be used at a time; the system is a time-division multiplexing system. In a system with many lasers of different wavelength, the signal of each wavelength must be differentiated or discriminated from the others, and the method for discrimination can be time division multiplexing or frequency division multiplexing, in which each laser is modulated with a unique frequency. The receiver distinguishes laser signals by correlating a signal to a specific time slot in time division multiplexing or to a specific known frequency in frequency division multiplexing. The drawback is low efficiency and high cost.

Ladar systems are disclosed in the following U.S. published patent applications, the disclosures of which are incorporated into this patent by this reference:

20030137647 Hybrid optical correlator/digital processor for target detection and discrimination 20030076485 Ladar system for detecting objects 20030067537 System and method for three-dimensional data acquisition 20030052169 Planar laser illumination and imaging (PLIIM) based camera system for producing high-resolution 3-D images of moving 3-D objects 20020131163 Optical amplifier employing an active doped unitary amplifier In a typical diffuse optical tomography system, the function of a system is to determine the spatial profile of the absorption and scattering coefficients of a medium, and reconstruct an image of the medium. The prior art approach is to have a single source location at a time, and all receivers measure the signal in parallel. Continuous wave, frequency domain, and time domain methods are known and used in the prior art for signal modulation and measurement. In each of the three methods, the transmitter is a single laser of one wavelength, or multiple lasers of different wavelengths. An essential aspect of diffuse optical tomography is the location of the transmitter and receiver relative to the subject of interest. If the transmitter needs to move from one location to another, the prior art method is to optically switch the transmitter light beam from one port to another port that leads the beam to another location. If the transmitter needs to change the wavelength, the input laser must be tuned from one wavelength to another. When multiple lasers of different wavelengths are used, the lasers must take turns to be turned on and off, in order to change the transmitter output wavelength. The transmitter is operated in the time-division-multiplexing mode. The drawback is that the switching time is limited by the speed of the optical switches employed. Diffuse optical tomography and other optical systems can be found in U.S. Pat. Nos. 6,577,884; 6,516,214; 5,853,370; 5,353,799; 5,421,329; 5,282,467; 5,782,237; 5,553,614; 5,792,051; 5,902,235; 5,795,292; 5,697,367; 5,584,296; 5,482,034; 5,477,853; 5,465,714; 5,217,013; 5,140,989; 5,139,025; 4,817,623; 4,768,516; 4,725,147; 4,570,638; and 5,779,631, the disclosures of which are incorporated into this patent by this reference.

Opto-electronic systems and methods, and related devices, for remote detection of physical magnitudes, are disclosed in the following U.S. patents, the disclosures of which are incorporated into this patent by this reference:

U.S. Pat. No. 5,774,215 Reduced complexity fourier transform spectrometer

U.S. Pat. No. 5,564,832 Birefringent active fiber laser sensor

U.S. Pat. No. 5,513,913 Active multipoint fiber laser sensor

U.S. Pat. No. 5,381,010 Periodically alternating path and alternating wavelength bridges for quantitative and ultrasensitive measurement of vapor concentration U.S. Pat. No. 5,307,146 Dual-wavelength photometer and fiber optic sensor probe U.S. Pat. No. 5,299,869 Laser diode temperature sensing system U.S. Pat. No. 5,200,796 Method and apparatus for detecting and measuring a physical magnitude U.S. Pat. No. 5,191,458 Optical electronic multiplexing reflection sensor system U.S. Pat. No. 5,179,424 Optoelectronic apparatus for the remote measuring of a physical magnitude U.S. Pat. No. 4,814,604 Opto-electronic method and system for remote detection of physical magnitudes Many optical sensing systems require multiple detections of several properties of the target. Using the existing techniques often results in high cost from time-consuming optical sensing. What is needed is a robust, highly efficient, and low cost method capable of simultaneous detection of target properties.

BRIEF SUMMARY OF THE INVENTION

A method for determining optical properties of a target, using a plurality of transmitters for transmitting signals at the target, and a plurality of receivers for detecting reflected signals from the target, comprising the steps of: a) transmitting radiation signals with a plurality of wavelengths at the target; b) detecting trace reflected radiation signals from the target by at least one of the plurality of receivers; c) modulating the plurality of transmitters with a waveform for generating transmitter modulation codes; d) mixing the transmitter modulation codes with the trace reflected radiation signals to generate total signals; e) transmitting the total signals at the target; f) simultaneously detecting reflected total signals from the target by at least one of the plurality of receivers; g) decoding the known waveform of each transmitter of the plurality of transmitters for determining each transmitter's signal; h) dispreading the reflected total signals with a device capable of bipolar signal processing to generate equivalent decoding functions with orthogonality; i) digitizing the reflected total signals with an analog-digital converter to generate digitized signals, and integrating the digitized signals with the decoding functions; and j) determining the optical properties of the target, selected from a group consisting of optical power, time delay, polarization, and beam, using a time-division multiplexing procedure of the plurality of transmitters for accurate determination of optical power.

In another feature of the invention, the modulation can be an in-phase modulation, an intensity modulation, or a combination of both. In yet another feature of the method of the present invention, at least one receiver concurrently detects signals from multiple transmitters. In yet another feature of the invention, a code-division multiplexing technique measures and distinguishes the optical radiation from transmitters. The code-division multiplexing modulation offers the advantage of less signal processing and computation. This invention offers the advantages of compactness, high efficiency, low cost, and is robust against jamming, interference, and impulse noises.

DETAILED DESCRIPTION OF THE INVENTION

Figure 1:
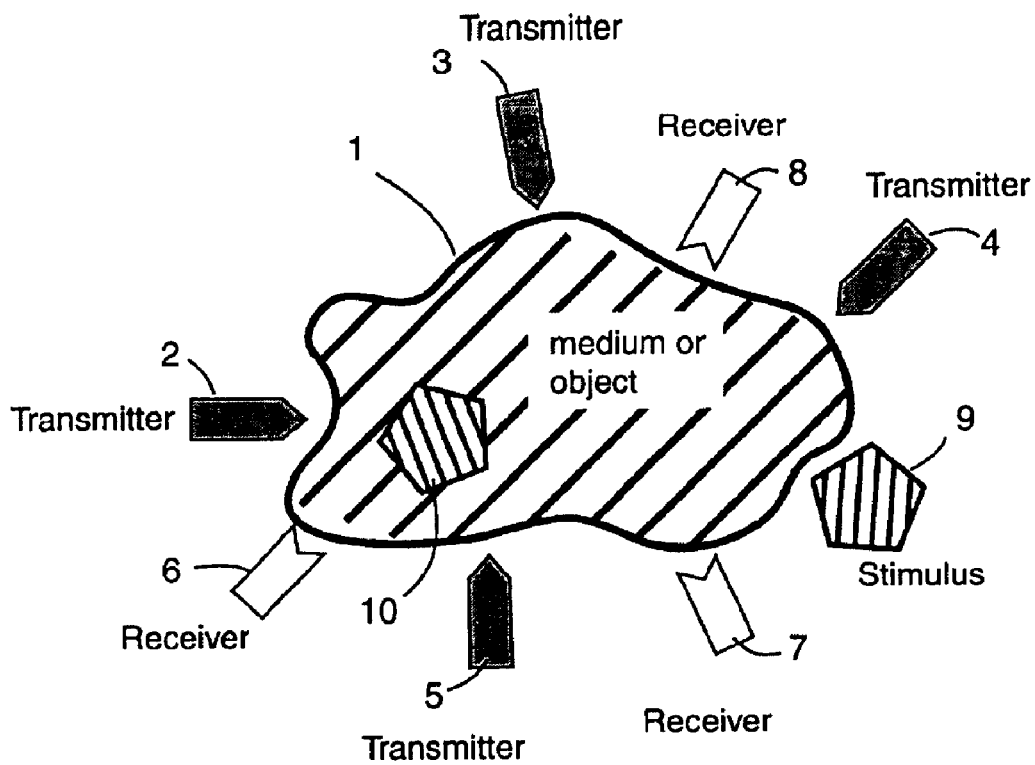
FIG. 1A illustrates the system of the invention with an object to be measured.
FIG. 1B is general schematic of the system.
Figure 1:
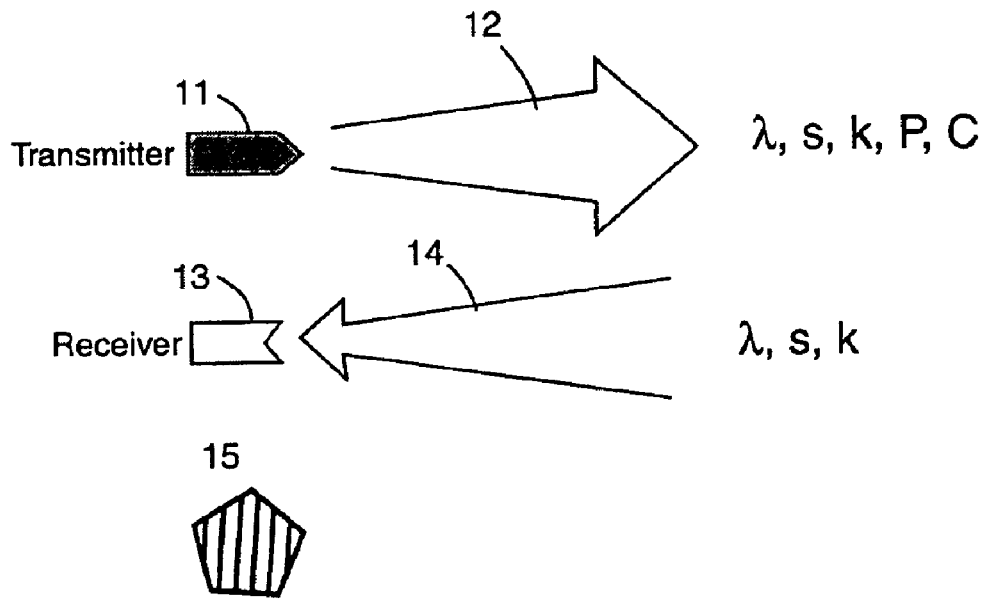

In FIG. 1A, an object or target 1, whose optical properties are to be measured, is surrounded by the system of the present invention, which includes transmitters 2, 3, 4, and 5, and receivers 6, 7, 8, and 9. In addition to the transmitters and receivers, the system may include other non-optical devices that can stimulate the target 1, such as sound transducers or chemicals. The receivers distinguish the signals from the transmitters by code division multiplexing.

Referring now to FIG. 1B, a transmitter 11 emits optical radiation 12 that has a spectral property e, a polarization property s, a beam property k, a power property P, and a modulation waveform C. Likewise, a receiver 13 detects incoming optical radiation 14 that also has properties ë, s, and k.

Figure 2:
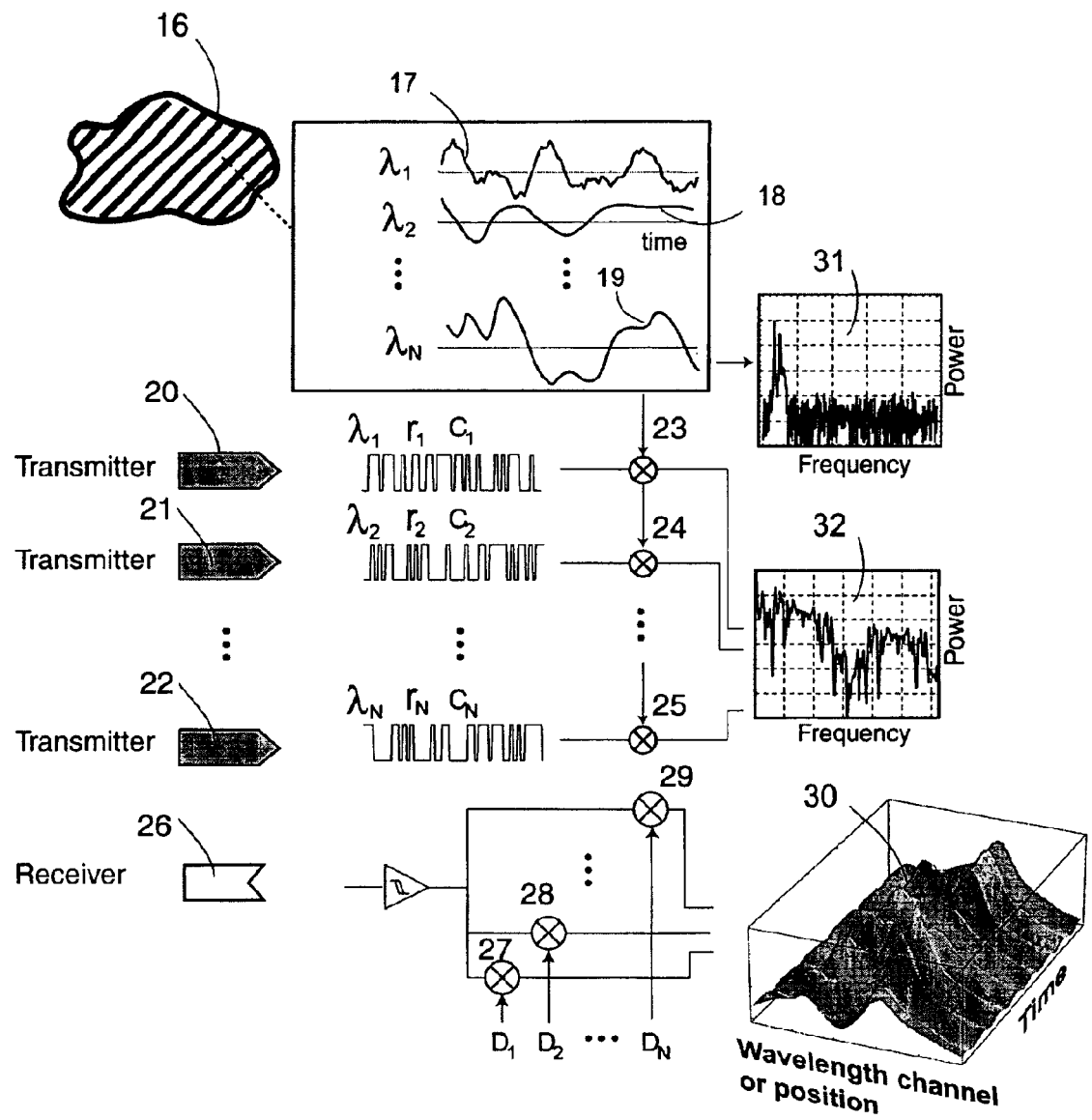
FIG. 2 shows the application of code-division multiplexing for measuring the time dependent optical properties of a target.

Referring now to FIG. 2, the method of the invention requires that at least one receiver can respond to a plurality of transmitter signals. The optical reflected trace radiation signals 17, 18, and 19 detected from a target 16 have both multi-spectral and temporal signatures. Each optical reflected trace radiation signal 17, 18, and 19 represents a time-dependent absorption property of the target at wavelengths $\ddot{e}_1, \ddot{e}_2 \ldots \ddot{e}_N$, which correspond to the wavelengths of transmitters 20, 21, 22. A code-division multiplexing technique allows a receiver 26 to measure all trace radiation signals 17, 18, 19 simultaneously. U.S. Pat. No. 5,668,806 to Arai, et al. discloses a code-division multiplexing technique, which patent is incorporated into this patent by this reference. The code-division multiplexing technique modulates each transmitter 20, 21, 22 with a unique high-bandwidth pseudo-noise code $C_k$, which, after transmitted at the target 1, is mixed with the reflected trace radiation signals 17, 18, and 19 to generate reflected total signals 23, 24, 25. The receiver 26 detects the resulting reflected total signals 23, 24, 25, which are products of the transmitter modulation code and the reflected trace radiation signals 17, 18, and 19. The method is applicable to any number of receivers. The receiver 26 detects all the reflected total signals, and simultaneously decodes them using decoders 27, 28, and 29, with all transmitter modulations $C_k$ and with known decode functions $D_k$, where k is an integer from 1 to N. The output of the decoding by the receiver 26 is the target temporal and spectral signature 30 that is plotted versus transmitter properties.

The code-division multiplexing technique is applied with modulation that has a bandwidth much larger than that of the trace radiation of the target. The resulting reflected total signals 23, 24, 25 have a total bandwidth shown in graph 32 that is also much higher than the total bandwidth of the reflected trace radiation signals 17, 18, and 19 shown in graph 31. Spreading the signal power over a wide spectrum provides the advantage of no single noise source being able to affect a particular frequency band.

In the method of the present invention, at least one receiver responds to two or more transmitter signals. The code-division multiplexing technique allows the extraction of an individual signal from the total signals by applying a decoding function. Thus, the preferred embodiment of the present invention is an orthogonality of code function and decoding function.

Figure 3A:
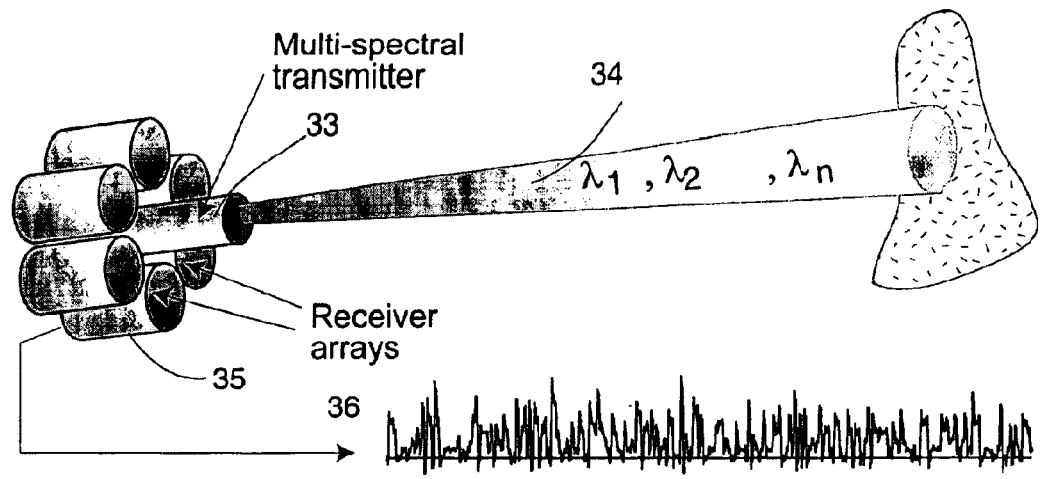
FIG. 3 illustrates a multi-wavelength ladar using the method of the present invention.
Figure 3B:
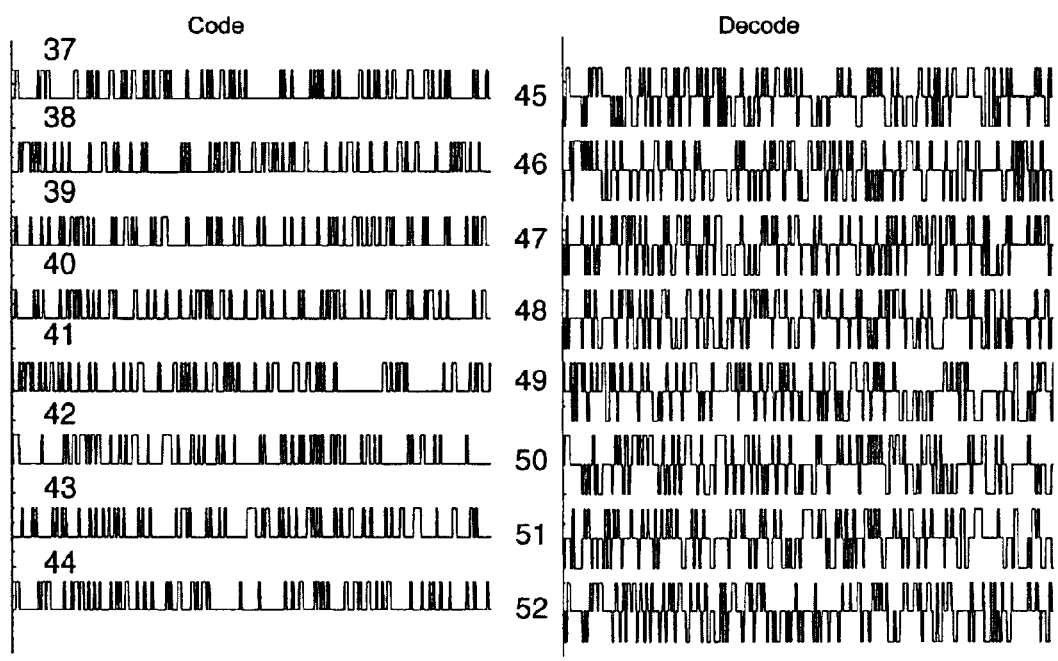

Referring now to FIG. 3A, for remote sensing of an object or a gas, the method and system of the present invention is used with a multi-wavelength laser transmitter 33. The transmitter 33 is a combination of eight lasers with different wavelengths 34. Each laser is intensity-modulated with a unique code 37, 38, 39, 40, 41, 42, 43, 44. The eight different signals of the codes 37, 38, 39, 40, 41, 42, 43, 44 are illustrated in FIG. 3B. For a receiver 35, a signal 36 is a linear sum of the return signals from all eight lasers, including noise. The signal 36 is digitized with an analog-digital-converter, and the digitized signals are integrated with eight decode functions. The eight codes 37, 38, 39, 40, 41, 42, 43, 44 and the eight decode functions 45, 46, 47, 48, 49, 50, 51, 52, also illustrated in FIG. 3B, are orthogonal. In the intensity-modulation, the signal is always positive, but with digitization, the decode function can be designed to be bipolar, assuming the values of [−1,0,1].

Figure 4A:
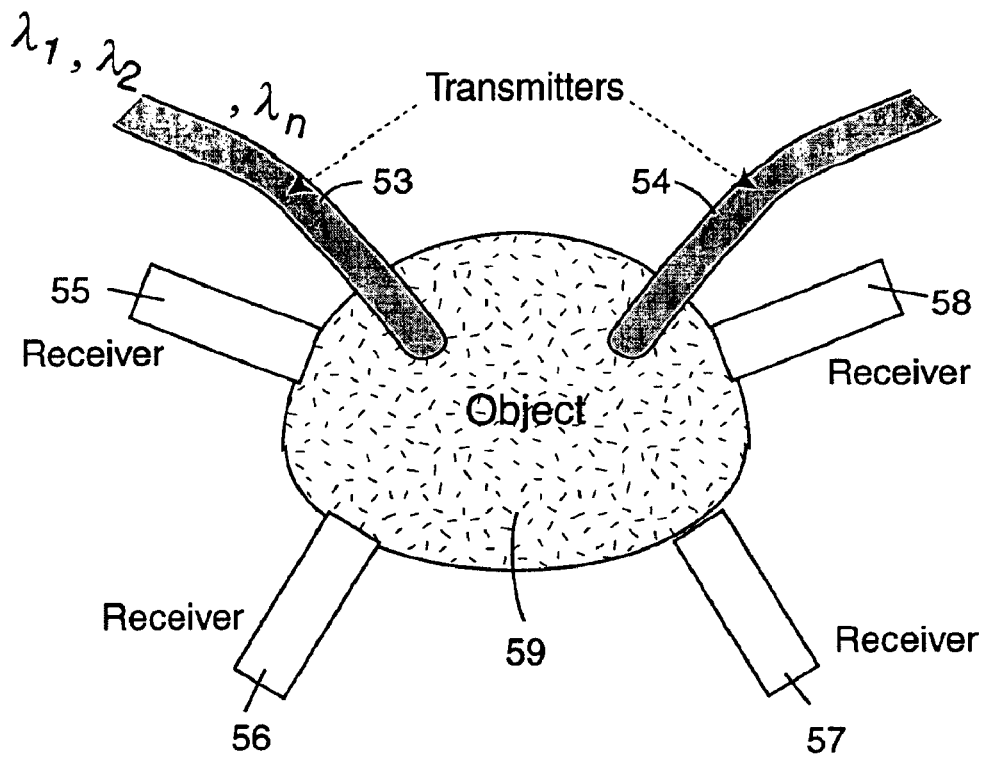
FIG. 4A illustrates the preferred embodiment of the invention with an optical diffuse tomography device, having two transmitters at different locations, each with multiple wavelengths, and four receivers.

Referring now to FIG. 4A, another embodiment of the method of the present invention uses a first code-division multiplexing in combination with a second code-division multiplexing. Each of two transmitters 53, 54 at different locations emits a plurality of wavelengths at an object, or target 59. Four receivers 55, 56, 57, 58 are set at different locations surrounding the object. The invention determines the optical properties of the target 59.

Figure 4B:
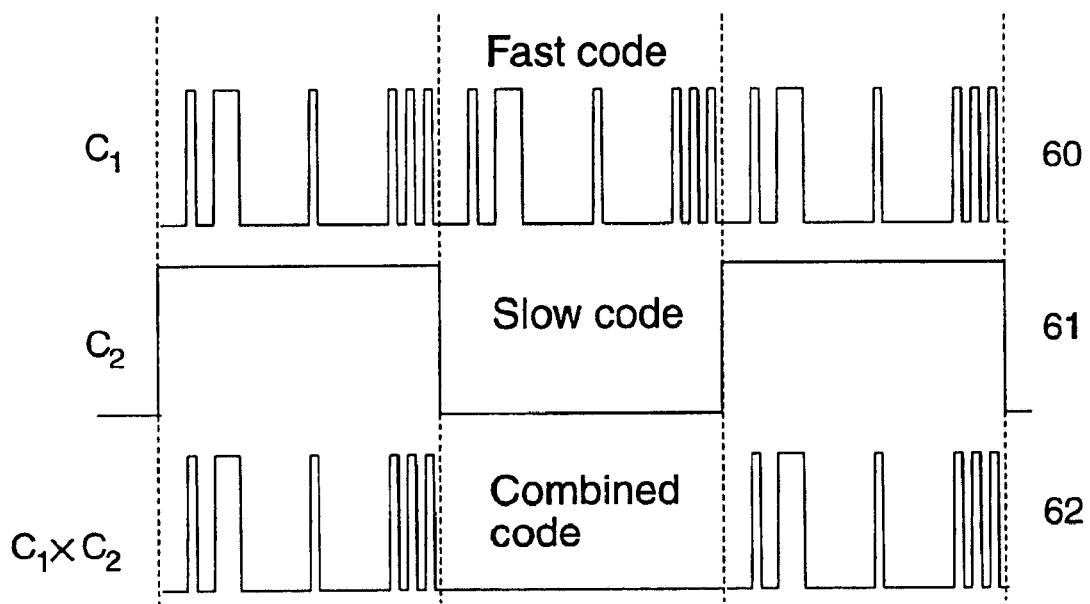
FIG. 4B illustrates the method of the present invention of combining codes for distinguishing transmitter location and wavelength as depicted in FIG. 4A.

Referring now to FIG. 4B, each laser of wavelength $\ddot{e}_k$ at location j is modulated with two codes that belong to two different sets of codes. A first set of code $C_1$ 60 is used to modulate at high bandwidth, and a second set of code $C_2$ 61 is used to modulate at low bandwidth, such that the duration of each section of code 2 is equal to the entire code sequence of code 1, as illustrated in the combined code 62. The decoding process of received signals at the receivers 55, 56, 57, 58 consists of two consecutive integrations. An alternative embodiment of the invention uses a single large code set instead of two nested code sets, and assigns one code to each pair to modulate the laser with wavelength $\ddot{e}_k$ at location j.

The embodiments of the invention in FIGS. 3 and 4 measure optical power that is transmitted, reflected, diffused, or scattered by the target. An alternate embodiment of the invention measures time delay of the optical radiation. The method of the present invention may also be used with systems that have a plurality of transmitters that require the measurement and distinction of both optical power and time delay from the different transmitters. The time-delay can be measured with numerous prior art techniques for code phasing involving only one transmitter signal. The invention uses existing, known techniques to determine the time delay, which can be used for subsequent accurate measurement of optical power based on code-division multiplexing technique. The invention employs intensity modulation. However, any modulation of electromagnetic wave is applicable to the method of the invention, including the modulation of optical carrier phase and polarization, and a combination thereof. The selection of a modulation type depends on the specific needs and designs of optical sensing systems.

Figure 5:
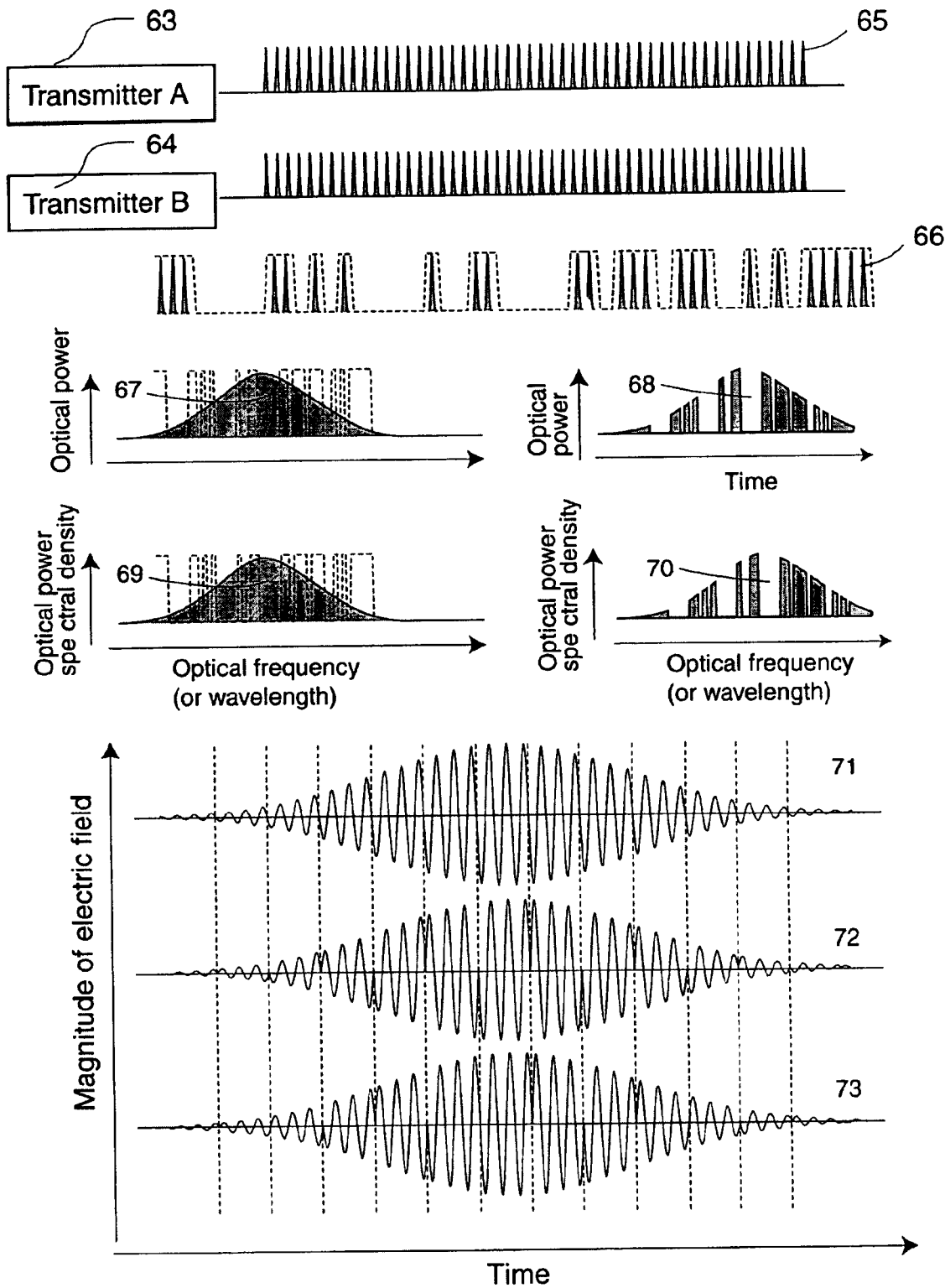
FIG. 5 illustrates the method of the present invention, using a code-division multiplexing technique to pulse lasers.

Referring now to FIG. 5, a pulse-laser transmitter 63 and a pulse-laser transmitter 64 each outputs a series of periodic pulses 65, such as the output of a periodic Q-switched or mode-locked laser. If the chip duration of a code is longer than a pulse, the application of DSSS modulation gives a typical signal 66. U.S. Pat. No. 5,555,268 to Fattouche, et al. discloses a modulation scheme called "multicode direct sequence spread spectrum" ("MC-DSSS"), which patent is incorporated into this patent by this reference. It is also possible to encode DSSS within the signal 66 using ultra fast optoelectronic devices for encoding/decoding to give a signal 67. The code-division multiplexing encoding can also be performed in the optical frequency domain. The laser pulse is represented in the frequency 69, which has spectrum 70 after encoding. A laser pulse 71 is encoded with $\ddot{o}$ phase shift, resulting in a pulse 72 with one code and a pulse 73 with another code. The vertical dash lines indicate the length of a chip, which is usually much larger than several periods of optical wave. Each of the two different code pulses 72 and 73 is used to distinguish each pulse from transmitters 63 and 64. If the encoding is performed with a programmable photonic encoder, each pulse from the same transmitter is distinguishable.

What is claimed is:

1. A method for determining optical properties of a target, using a plurality of transmitters for transmitting signals at the target, and a plurality of receivers for detecting reflected signals from the target, comprises the steps of:
   a. transmitting radiation signals with a plurality of wavelengths at the target;
   b. detecting reflected trace radiation signals from the target;
   c. modulating the plurality of transmitters with a waveform for generating transmitter modulation codes;
   d. mixing the transmitter modulation codes with the reflected trace radiation signals to generate total signals;
   e. transmitting the total signals at the target;
   f. detecting reflected total signals from the target;
   g. decoding the known waveform of each transmitter of the plurality of transmitters for determining each transmitter's signal;
   h. dispreading the reflected total signals with a device capable of bipolar signal processing to generate equivalent decoding functions with orthogonality;
   i. digitizing the reflected total signals with an analog-digital converter to generate digitized signals;
   j. integrating the digitized signals with the decoding functions to extract individual signals from the total signals; and
   k. determining the optical properties of the target from the individual signals, selected from a group consisting of optical power, time delay, polarization, and beam.

2. The method of claim 1, further comprising using at least one other non-optical device for stimulating said target.

3. The method of claim 1, wherein the trace radiation signals comprise signals transmitted, reflected, diffused, or scattered by the target.

4. The method of claim 1, wherein the target is selected from a group consisting of an environment, a medium, an object, and a combination thereof.

5. The method of claim 1, wherein the radiation signals are an optical wave or a sound wave.

6. The method of claim 1, wherein the bandwidth of transmitter modulation codes is larger than that of the trace radiation signals.

7. The method of claim 1, wherein the step of modulating consists of in-phase modulating, intensity modulating, and combination thereof by the waveform.

8. The method of claim 1, wherein the waveform is selected from a group consisting of a set of codes and a plurality of sets of codes from code-division multiplexing in nested combination with a multiplexing technique that is not code-division multiplexing.

9. The method of claim 1, wherein the transmitters are modulated only with information known to the receivers.

10. The method of claim 1, further comprising measuring the optical properties selected from a group consisting of optical power and time delay.

* * * * *